US008821432B2

(12) United States Patent
Unverdorben

(10) Patent No.: US 8,821,432 B2
(45) Date of Patent: Sep. 2, 2014

(54) SPLIT AND MULTIPLE AIR BUBBLE SENSORS FOR AUTOMATED INFUSION SYSTEMS

(75) Inventor: Martin Unverdorben, Pottstown, PA (US)

(73) Assignee: B. Braun Medical Inc., Bethlehem, PA (US)

( * ) Notice: Subject to any disclaimer, the term of this patent is extended or adjusted under 35 U.S.C. 154(b) by 193 days.

(21) Appl. No.: 13/408,201

(22) Filed: Feb. 29, 2012

(65) Prior Publication Data
US 2013/0226129 A1    Aug. 29, 2013

(51) Int. Cl.
*A61M 31/00*    (2006.01)
*F04B 49/00*    (2006.01)

(52) U.S. Cl.
USPC ................................ 604/65; 604/67; 417/282

(58) Field of Classification Search
USPC ................ 604/65–67, 151; 417/282
See application file for complete search history.

(56) References Cited

U.S. PATENT DOCUMENTS

| | | | |
|---|---|---|---|
| 4,114,144 A | 9/1978 | Hyman | |
| 4,366,384 A | 12/1982 | Jensen | |
| 4,367,736 A * | 1/1983 | Gupton | 604/30 |
| 5,260,665 A | 11/1993 | Goldberg et al. | |
| 5,382,232 A | 1/1995 | Hague et al. | |
| 5,394,732 A | 3/1995 | Johnson et al. | |
| 5,536,471 A * | 7/1996 | Clark et al. | 422/63 |
| 6,408,679 B1 | 6/2002 | Kline-Schoder et al. | |
| 6,616,633 B1 | 9/2003 | Butterfield et al. | |
| 7,141,037 B2 | 11/2006 | Butterfield et al. | |
| 7,338,470 B2 * | 3/2008 | Katz et al. | 604/122 |
| 7,981,082 B2 | 7/2011 | Wang et al. | |
| 8,622,979 B2 * | 1/2014 | Hungerford et al. | 604/253 |

FOREIGN PATENT DOCUMENTS

| | | | | |
|---|---|---|---|---|
| AU | WO 81/00519 | * | 3/1981 | 604/65 |
| EP | 0643301 A1 | | 3/1995 | |
| FR | 2361644 A1 | | 3/1978 | |
| WO | WO2005/118051 A2 | | 12/2005 | |
| WO | WO 2009/026420 A1 | | 2/2009 | |

OTHER PUBLICATIONS

International Search Report dated May 7, 2013, application No. PCT/US2013/027877.
International Search Report dated May 10, 2013, application No. PCT/US2013/027931.

* cited by examiner

*Primary Examiner* — Nicholas Lucchesi
*Assistant Examiner* — Rebecca E Eisenberg
(74) *Attorney, Agent, or Firm* — RatnerPrestia

(57) ABSTRACT

Systems and methods for sensing bubbles during fluid infusion are disclosed. An infusion device comprises a pathway, at least one pump adjacent the pathway, first and second bubble sensors positioned adjacent the pathway, and a processor. The pathway is adapted to receive tubing. The pump alters the pathway to pump fluid through the tubing when the tubing is received in the pathway. The second bubble sensor is spaced from the first bubble sensor. The first and second bubble sensors are configured to detect a bubble in the fluid being pumped through the tubing. The processor is programmed to determine that the first bubble sensor detects a bubble, determine whether the second bubble sensor detects a bubble, and to generate an alarm condition only when the first bubble sensor and the second bubble sensor detect the same bubble.

24 Claims, 3 Drawing Sheets

SPLIT AND MULTIPLE AIR BUBBLE SENSORS FOR AUTOMATED INFUSION SYSTEMS

FIELD OF THE INVENTION

The present invention relates generally to infusion systems and, more particularly, to systems and methods for sensing bubbles during fluid infusion.

BACKGROUND OF THE INVENTION

During medical treatment it is often necessary to infuse fluids, such as medication or nutrients, into a patient's circulatory system. Conventionally, infusions are performed using infusion devices, which may include one or several pumps to infuse fluid to the patient at a predetermined rate and time. These infusion devices may be programmed according to predetermined handwritten or electronic infusion protocols, which are based, for example, on the fluid to be infused and/or the particular patient.

For safety purposes in a medical treatment setting, it is often necessary to identify air bubbles that form in the fluid or from the outside and penetrate into the fluid being infused. Accordingly, conventional infusion devices include sensors configured to generate an alarm when air bubbles are detected. However, these conventional sensors may be improperly triggered by "micro-bubbles" (which are not considered harmful to the patient) that cling to the inside of the infusion tubing. Accordingly, improved systems and methods for sensing bubbles during fluid infusion are desired.

SUMMARY OF THE INVENTION

Aspects of the present invention relate to systems and methods for sensing bubbles during fluid infusion.

In accordance with one aspect of the present invention, an infusion device is disclosed. The infusion device comprises a pathway adapted to receive tubing, at least one pump adjacent the pathway, first and second bubble sensors positioned adjacent the pathway, and at least one processor. The at least one pump alters the pathway to pump fluid through the tubing when the tubing is received in the pathway. The second bubble sensor is spaced from the first bubble sensor. The first and second bubble sensors are configured to detect a bubble in the fluid being pumped through the tubing. The at least one processor is in communication with the first and second bubble sensors. The at least one processor is programmed to determine that the first bubble sensor detects at least one bubble, determine whether the second bubble sensor detects at least one bubble, and to generate an alarm condition only when the first bubble sensor and the second bubble sensor detect the same at least one bubble. The second bubble sensor may be removably connected to the infusion device. The second bubble sensor may be spaced from the first bubble sensor in an axial or circumferential direction relative to the pathway. The at least one processor may be further programmed to calculate a time lag between the first bubble sensor and the second bubble sensor. The at least one processor may generate the alarm condition only when both the first bubble sensor and the second bubble sensor detect at least one bubble having a volume exceeding a preselected volume.

In accordance with another aspect of the present invention, a sensor element for an infusion device is disclosed. The sensor element comprises a first bubble sensor and a second bubble sensor. The first bubble sensor is adapted to be positioned adjacent the pathway of the infusion device. The second bubble sensor is adapted to be positioned adjacent the pathway of the infusion device and spaced from the first bubble sensor. The first and second bubble sensors are configured to detect at least one bubble in the fluid being pumped through tubing received in the pathway. The first and second bubble sensors are configured to be connected to at least one processor of the infusion device in order to send sensed bubble data to the infusion device. The second bubble sensor may be spaced from the first bubble sensor in an axial or circumferential direction relative to the pathway.

In accordance with yet another aspect of the present invention, a method for sensing bubbles during fluid infusion is disclosed. The method comprises the step of pumping fluid through tubing with at least one pump of an infusion device, detecting at least one bubble in the fluid being pumped through the tubing with a first bubble sensor, detecting at least one bubble in the fluid being pumped through the tubing with a second bubble sensor spaced from the first bubble sensor, and generating an alarm condition only when the first bubble sensor and the second bubble sensor detect the same at least one bubble. The method may also comprise calculating a time lag between the first bubble sensor and the second bubble sensor. The generating step may comprise generating the alarm condition only when both the first bubble sensor and the second bubble sensor detect at least one bubble having a volume exceeding a preselected volume. More than two (multiple) bubble sensors may be used, including a sensor located outside of the infusion device.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. This emphasizes that according to common practice, the various features of the drawings are not drawn to scale unless otherwise indicated. To the contrary, the dimensions of the various features may be expanded or reduced for clarity. Included in the drawings are the following figures.

DETAILED DESCRIPTION OF THE INVENTION

The exemplary systems and methods disclosed herein are directed toward infusing a fluid to a patient. The disclosed embodiments are usable in systems where it is necessary or desirable to accurately detect the formation of bubbles in or the penetration of bubbles into the fluid being infused. In particular, the disclosed embodiments may be particularly suitable for use in preventing improper alarms from being triggered due to the presence of stationary micro-bubbles in the fluid being infused.

Generally, the embodiments described herein include multiple bubble sensors positioned at various points along a fluid pathway of an infusion device. If a first bubble sensor detects a bubble in the fluid during infusion, the infusion device checks a second bubble sensor at a different point to see if the same bubble is detected. The second bubble sensor may be axially or circumferentially spaced from the first bubble sensor. If the same bubble is detected, the device may generate an alarm indicating that the bubble must be cleared. However, if the first sensor is triggered by micro-bubbles that cling to the wall of the tube adjacent the first sensor, and do not pose any risk to the patient, those micro-bubbles will not be seen by the second sensor, and accordingly, the alarm will not be generated unless preselected to alarm.

Figure 1:
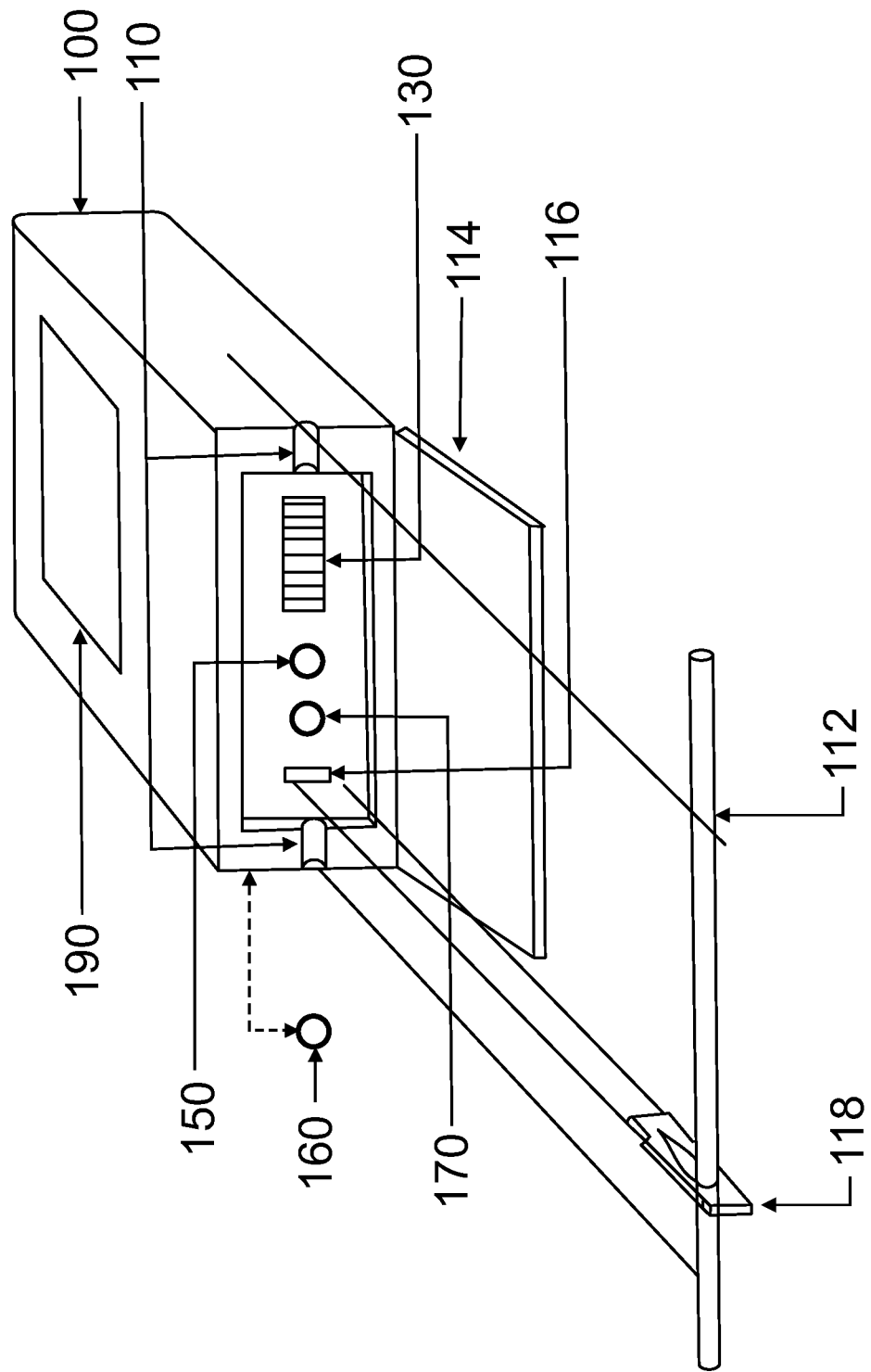
FIG. 1 is a diagram illustrating an exemplary infusion device in accordance with aspects of the present invention.

Referring now to the drawings, FIG. 1 illustrates an exemplary infusion device 100 in accordance with aspects of the present invention. Infusion device 100 is configured to infuse fluid (e.g., medication) to a patient. As a general overview, infusion device 100 includes a pathway 110, a pump 130, bubble sensors 150, 160, and 170, and at least one processor 190. The location of bubble sensors 150, 160, and 170 are necessarily different from each other. Additional details of infusion device 100 are described herein.

Pathway 110 is adapted to receive a pump set or a mock pump set. The pump set includes tubing 112 configured to receive fluid from a fluid container (not shown). As used herein, the term "pathway" refers to any structure (such as a slot, retainer, or groove) adapted to receive and/or retain tubing 112 of the pump set. Pathway 110 may include a guide adapted to secure tubing 112 of the pump set in a desired location and orientation within infusion device 100. In an exemplary embodiment, infusion device 100 includes a door 114 adapted to secure pump set tubing 112 within pathway 110 when closed, as shown in FIG. 1. Infusion device 100 may also include a recess 116 adapted to receive an attachment 118 (such as, but not limited to, an anti-free flow clamp) of the pump set. Recess 116 may be usable to properly key the pump set tubing 112 within pathway 110 (i.e. ensure that the pump set is facing a proper direction).

Pump 130 is positioned adjacent pathway 110. Pump 130 is adapted to alter pathway 110 in order to pump fluid through pump set tubing 112 when the tubing 112 is received in pathway 110. In an exemplary embodiment, pump 130 is a peristaltic pump. Suitable pumps for use as an infusion pump 130 will be known to one of ordinary skill in the art from the description herein.

Bubble sensors 150, 160, and 170 are positioned adjacent pathway 110 of infusion device 100. Bubble sensor 170 is spaced from bubble sensor 150 relative to pathway 110. Bubble sensor 170 may be axially spaced (e.g. positioned downstream) or circumferentially spaced (e.g. on another side of tubing 112) relative to bubble sensor 150. As shown in FIG. 1, bubble sensor 170 is positioned downstream from bubble sensor 150. However, bubble sensor 170 may be positioned anywhere within or outside of infusion device 100. For example, bubble sensor 170 may be circumferentially spaced from bubble sensor 150 around tubing 112, e.g., by approximately 90°. Bubble sensors 150 and 170 are configured to detect bubbles in the fluid being pumped through the tubing 112 by pump 130. Suitable bubble sensors for use as bubble sensors 150 and 170 will be known to one of ordinary skill in the art from the description herein.

Figure 2:
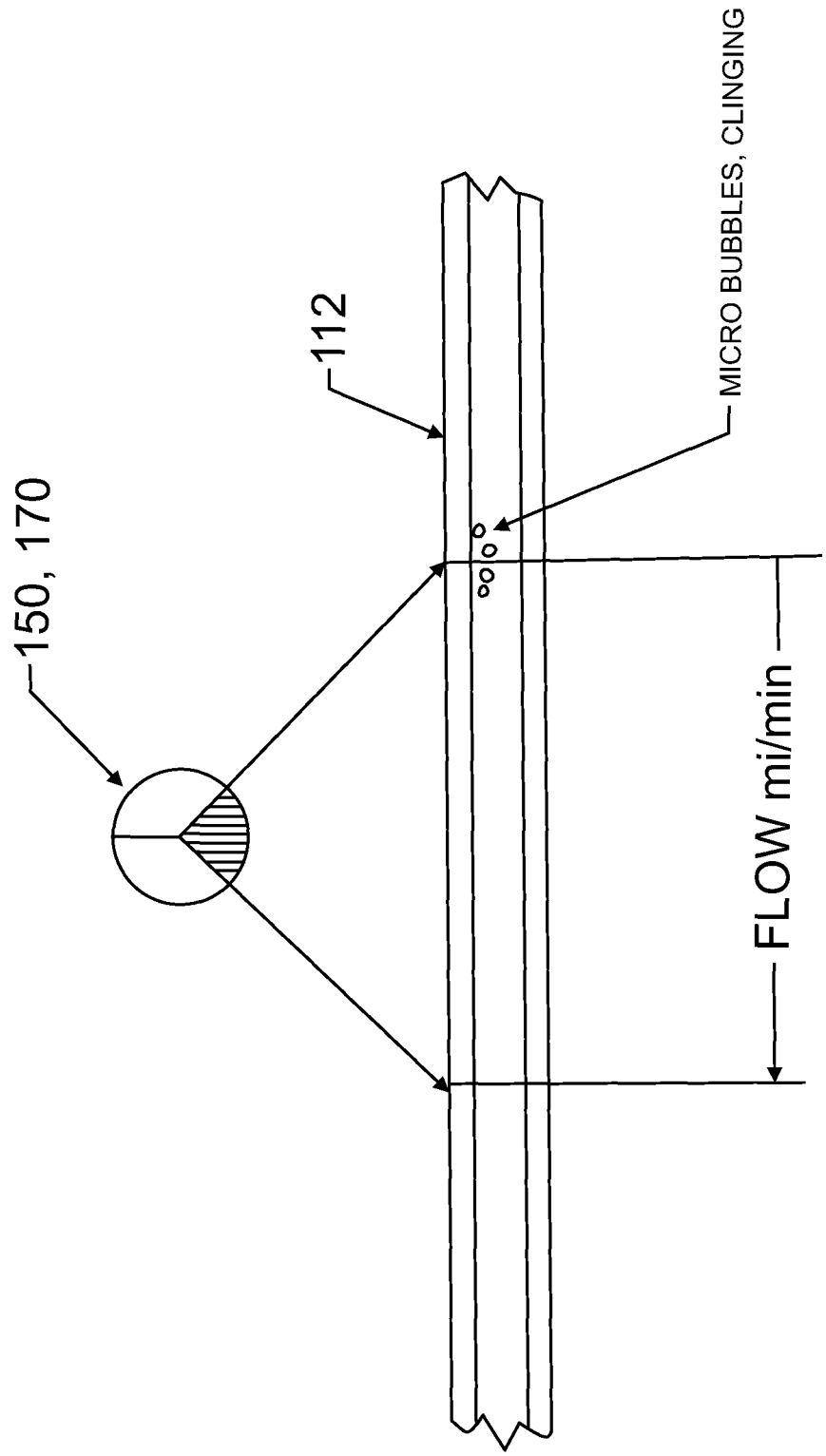
FIG. 2 is a diagram illustrating exemplary sensors of the infusion device of FIG. 1.

In one exemplary embodiment, bubble sensors 150, 160, and 170 are part of two or more separate, distinct sensing devices, i.e., two separate sensors. In this embodiment, bubble sensors 150 and 170 may be incorporated within a housing of infusion device 100, while bubble sensor 160 is a separate sensor that is removably connected to the infusion device 100. In another exemplary embodiment, bubble sensor 160 may be omitted, and bubble sensors 150 and 170 may be part of a single sensing device, as shown in FIG. 2. In this embodiment, a single sensing device may be used that employs an optical beam to detect bubbles in tubing 112. The single sensing device may include a beam splitter for splitting the optical beam into two separate and distinct beams, which may then be guided to the appropriate positions on tubing 112. A diagram of exemplary sensors employing a split beam for sensing bubbles is illustrated in FIG. 2.

Processor 190 controls the operation of infusion device 100. At least one processor 190 is in communication with pump 130 and bubble sensors 150 and 170. Processor 190 controls the programming of infusion device 100 with the at least one infusion protocol, and coordinates the operation of pump 130 in accordance with the at least one infusion protocol. As is explained in greater detail below, processor 190 monitors data from bubble sensors 150 and 170 to determine whether there are bubbles in the fluid and, if present, the sizes thereof and total volume over time being pumped by pump 130.

While only a single processor 190 is illustrated in FIG. 1, it will be understood that the invention is not so limited. Infusion device 100 may include any number of processors configured to perform the operations described herein, as would be understood by one of ordinary skill in the art. As used herein, the term "processor" is intended to encompass a single processing element or multiple processing elements, as necessary to perform the recited functions.

Processor 190 is configured to generate alarms based on the output of bubble sensors 150 and 170. In an exemplary embodiment, processor 190 is programmed to determine whether bubble sensor 150 has detected a bubble. When processor 190 determines that bubble sensor 150 has detected a bubble, processor 190 then determines whether bubble sensor 170 detects the same bubble. Processor 190 is programmed to generate an alarm condition only when bubble sensor 150 and bubble sensor 170 detect the same bubble. When processor 190 generates an alarm condition, it may be further programmed to deactivate pump 130 until the detected bubble is cleared from tubing 112.

In order to determine whether the bubbles sensed by multiple bubble sensors 150 and 170 are the same bubble, it may be necessary to calculate a time lag for data generated by bubble sensor 170 relative to bubble sensor 150 (i.e. when bubble sensors 170 is positioned downstream from bubble sensor 150). Accordingly, processor 190 may be programmed to calculate a time lag between bubble sensor 150 and bubble sensor 170. In an exemplary embodiment, processor 190 calculates the time lag based on the distance between bubble sensors 150 and 170, the infusion rate of the fluid, and an inner diameter of tubing 112, which may be available to processor 190 from the selected infusion protocol. By knowing the fluid flow rate and the inner diameter of tubing 112, processor 190 will be able to calculate how long it takes a bubble detected by bubble sensor 150 to reach bubble sensor 170, which corresponds to the time lag between bubble sensors 150 and 170. If bubble sensors 150 and 170 are circumferentially spaced (e.g. at a 90° angle from one another), then processor 190 may determine whether bubble sensors 150 and 170 have detected the same bubble based on whether measurements from bubble sensors 150 and 170 are within a preselected acceptable time difference.

It may be desirable to further limit the conditions under which processor 190 will generate an alarm condition. For example, processor 190 may be programmed to generate an alarm condition only when the bubbles detected by bubble sensors 150 and 170 are approximately the same size. For another example, processor 190 may be programmed to generate an alarm condition only when bubble sensors 150 and 170 detect at least one bubble having a volume exceeding a preselected volume. The preselected volume threshold may be surpassed by a single, large bubble, or may be surpassed by a plurality of bubbles having a combined volume exceeding the preselected volume. These limitations may be particularly suitable for preventing false or unnecessary alarms from being triggered by processor 190.

While infusion device 100 is described as including two bubble sensors 150 and 170, or a single split beam sensing device, it will be understood by one of ordinary skill in the art that the invention is not so limited. Infusion device 100 may include any number of bubble sensors positioned at substantially the same or different points along pathway 110 or outside of (and removably connected to) infusion device 100 in order to sense bubbles in tubing 112. The number and orientation of bubble sensors may be selected based on desired safety and cross-check concerns for detecting bubbles in the fluid being infused.

While the sensors 150 and 170 are described above as being formed integrally with infusion device 100, it will be understood by one of ordinary skill in the art that the invention is not so limited. The above described embodiments may also form the basis of a separate sensing element for modifying an existing infusion device to sense bubbles in fluid being infused, in accordance with aspects of the present invention. The sensing element includes a pair of bubble sensors adapted to be positioned adjacent the tubing pathway of an infusion device, e.g., by being coupled to the infusion device. When so coupled, one of the bubble sensors is spaced from the other bubble sensor (e.g. axially or circumferentially) relative to the pathway. As described above, the bubble sensors are configured to detect a bubble in the fluid being pumped through the tubing by the infusion device. The bubble sensors are further configured to be connected to one or several processors of the infusion device, in order to send sensed bubble data to the infusion device during operation. Suitable bubble sensors for use in the above-described stand-alone sensing element include any of the bubble sensors described above with respect to bubble sensors 150 and 170. Suitable infusion devices for use with a stand-alone sensing element as described above include, for example, the INFUSOMAT® SPACE infusion pump, provided by B. Braun Medical Inc., of Bethlehem, Pa.

Figure 3:
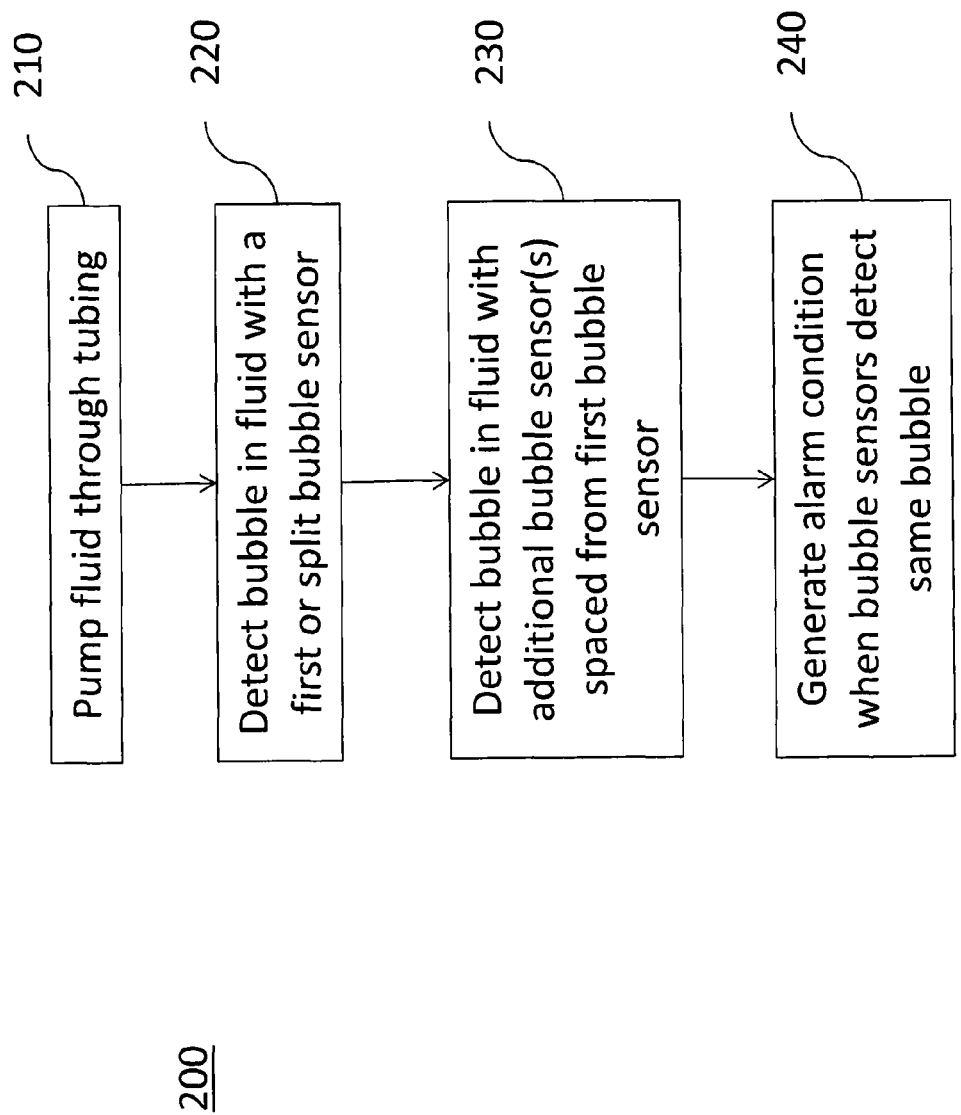
FIG. 3 is a diagram illustrating an exemplary method for sensing bubbles during fluid infusion in accordance with aspects of the present invention.

FIG. 3 shows an exemplary method 200 for sensing bubbles during fluid infusion in accordance with aspects of the present invention. As a general overview, method 200 includes pumping fluid through tubing, detecting a bubble with first and second bubble sensors, and generating an alarm condition. Additional details of method 200 are described herein with respect to the components of infusion device 100.

In step 210, fluid is pumped through tubing. In an exemplary embodiment, infusion device 100 is programmed with at least one infusion protocol. When tubing 112 is received within pathway 110, processor 190 controls pump 130 to pump fluid through tubing 112 in accordance with the at least one infusion protocol.

In step 220, a bubble is detected in the fluid at a first position. In an exemplary embodiment, bubble sensor 150 detects a bubble in the fluid being pumped through tubing 112. In step 230, a bubble is detected in the fluid at a different position from the first position. In an exemplary embodiment, bubble sensor 170 detects a bubble in the fluid at a position that is axially or circumferentially different from bubble sensor 150. In one embodiment, bubble sensor 170 may detect a bubble at a position downstream from bubble sensor 150. In another embodiment, bubble sensor 170 may detect a bubble at a position circumferentially rotated approximately 90° from bubble sensor 150. The detection of a bubble using bubble sensors 150 and 170 will be understood by one of ordinary skill in the art from the description herein.

In step 240, an alarm condition is generated. In an exemplary embodiment, processor 190 generates an alarm condition only when the first bubble sensor and the second bubble sensor detect the same bubble. As explained above, processor 190 may be programmed to generate an alarm condition only when the bubbles detected by bubble sensors 150 and 170 are approximately the same size. Processor 190 may be also programmed to generate an alarm condition only when one or more bubbles exceed a preselected volume threshold, unless otherwise preselected.

It will be understood that method 200 is not limited to the above steps, but may include alternative steps and additional steps, as would be understood by one of ordinary skill in the art from the description herein.

For one example, it may be necessary to calculate a time lag for data generated by bubble sensor 170 relative to bubble sensor 150. Accordingly, method 200 may include the step of calculating a time lag between the bubble sensors. In an exemplary embodiment, processor 190 calculates the time lag based on the infusion rate of the fluid and an inner diameter of tubing 112, which may be available to processor 190 from the selected infusion protocol.

For another example, it may be desirable to stop infusion when an alarm condition is generated. Accordingly, method 200 may include the step of deactivating the pump when the alarm condition is generated. In an exemplary embodiment, processor 190 is programmed to deactivate pump 130 when an alarm condition is generated, until either the detected bubble is cleared from tubing 112 and/or a user of infusion device 100 clears the alarm. The user of infusion device 100 may deactivate or clear the alarm whether the detected bubble is removed or not.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. An infusion device comprising:
   a pathway adapted to receive tubing;
   at least one pump adjacent the pathway, the at least one pump altering the pathway to pump fluid through the tubing when the tubing is received in the pathway; and
   a first bubble sensor positioned adjacent the pathway;
   a second bubble sensor positioned adjacent the pathway and spaced from the first bubble sensor, the first and second bubble sensors configured to detect a bubble in the fluid being pumped through the tubing; and
   at least one processor in communication with the first and second bubble sensors, the at least one processor programmed to determine that the first bubble sensor detects at least one bubble, determine whether the second bubble sensor detects at least one bubble, and to generate an alarm condition only when the first bubble sensor and the second bubble sensor detect the same at least one bubble,
   wherein the first and second bubble sensors are provided within a housing of the infusion device, and
   wherein the first and second bubble sensors comprise a single sensing device having a split sensing beam.

2. The infusion device of claim 1, wherein the second bubble sensor is spaced from the first bubble sensor in an axial direction relative to the pathway.

3. The infusion device of claim 1, wherein the second bubble sensor is spaced from the first bubble sensor in a circumferential direction relative to the pathway.

4. The infusion device of claim 3, wherein the second bubble sensor is circumferentially spaced from the first bubble sensor by approximately 90°.

5. The infusion device of claim 1, wherein the at least one processor is further programmed to calculate a time lag between the first bubble sensor and the second bubble sensor.

6. The infusion device of claim 5, wherein the at least one processor is programmed to calculate the time lag based on an infusion rate of the fluid and a diameter of the tubing.

7. The infusion device of claim 1, wherein the at least one processor generates the alarm condition only when both the first bubble sensor and the second bubble sensor detect at least one bubble of approximately the same size.

8. The infusion device of claim 1, wherein the at least one processor generates the alarm condition only when both the first bubble sensor and the second bubble sensor detect at least one bubble having a volume exceeding a preselected volume.

9. The infusion device of claim 8, wherein the at least one processor generates the alarm condition only when both the first bubble sensor and the second bubble sensor detect a plurality of bubbles having a combined volume exceeding the preselected volume.

10. The infusion device of claim 1, wherein the at least one processor is programmed to deactivate the pump when the alarm condition is generated.

11. A sensor element for an infusion device, the infusion device comprising a pathway and at least one pump, the sensor element comprising:
a first bubble sensor adapted to be positioned adjacent the pathway of the infusion device; and
a second bubble sensor adapted to be positioned adjacent the pathway of the infusion device and spaced from the first bubble sensor, the first and second bubble sensors configured to detect at least one bubble in the fluid being pumped through tubing received in the pathway, the first and second bubble sensors configured to be connected to at least one processor of the infusion device in order to send sensed bubble data to the infusion device,
wherein the first and second bubble sensors comprise a single sensing device having a split sensing beam.

12. The sensor element of claim 11, wherein the second bubble sensor is spaced from the first bubble sensor in an axial direction relative to the pathway.

13. The sensor element of claim 11, wherein the second bubble sensor is spaced from the first bubble sensor in a circumferential direction relative to the pathway.

14. The sensor element of claim 13, wherein the second bubble sensor is circumferentially spaced from the first bubble sensor by approximately 90°.

15. A method for sensing bubbles during fluid infusion comprising the step of:
pumping fluid through tubing with at least one pump of an infusion device;
detecting at least one bubble in the fluid being pumped through the tubing with a first bubble sensor;
detecting at least one bubble in the fluid being pumped through the tubing with a second bubble sensor spaced from the first bubble sensor; and
generating an alarm condition only when the first bubble sensor and the second bubble sensor detect the same at least one bubble,
wherein the first and second bubble sensors comprise a single sensing device having a split sensing beam.

16. The method of claim 15, further comprising the step of calculating a time lag between the first bubble sensor and the second bubble sensor.

17. The method of claim 16, wherein the calculating step comprises calculating the time lag based on an infusion rate of the fluid and a diameter of the tubing.

18. The method of claim 15, wherein the generating step comprises generating the alarm condition only when both the first bubble sensor and the second bubble sensor detect at least one bubble of approximately the same size.

19. The method of claim 15, wherein the generating step comprises generating the alarm condition only when both the first bubble sensor and the second bubble sensor detect at least one bubble having a volume exceeding a preselected volume.

20. The method of claim 19, wherein the generating step comprises the alarm condition only when both the first bubble sensor and the second bubble sensor detect a plurality of bubbles having a combined volume exceeding the preselected volume.

21. The method of claim 15, further comprising the step of deactivating the pump when the alarm condition is generated.

22. The method of claim 15, wherein the second detecting step comprises detecting a bubble with a second bubble sensor spaced from the first bubble sensor in an axial direction relative to the tubing.

23. The method of claim 15, wherein the second detecting step comprises detecting a bubble with a second bubble sensor spaced from the first bubble sensor in a circumferential direction relative to the tubing.

24. The method of claim 23, wherein the second bubble sensor is circumferentially spaced from the first bubble sensor by approximately 90°.

* * * * *